United States Patent [19]

Schwan

[11] 4,002,613

[45] Jan. 11, 1977

[54] 10-(3,4-DICHLOROBENZYL-)DIBENZ[B,F][1,4]OXAZEPIN-11-ONE

[75] Inventor: Thomas J. Schwan, Norwich, N.Y.

[73] Assignee: Morton-Norwich Products, Inc., Norwich, N.Y.

[22] Filed: Oct. 30, 1975

[21] Appl. No.: 627,225

[52] U.S. Cl. .................... 260/239.3 T; 424/244
[51] Int. Cl.$^2$ ........................ C07D 267/20
[58] Field of Search ............... 260/239.3 T

[56] References Cited

UNITED STATES PATENTS 3,423,402  1/1969  Nagarajan .................. 260/239.3 T

*Primary Examiner*—Henry R. Jiles
*Assistant Examiner*—Robert T. Bond
*Attorney, Agent, or Firm*—Anthony J. Franze

[57] ABSTRACT

The compound 10-(3,4-dichlorobenzyl)-dibenz[b,f][1,4]oxazepin-11-one possesses pharmacological activity as an antidepressant.

1 Claim, No Drawings

10-(3,4-DICHLOROBENZYL-DIBENZ[B,F][1,4]OX-AZEPIN-11-ONE

This invention relates to chemical compounds. In particular it is concerned with a compound of the formula:

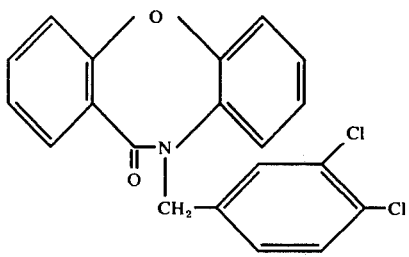

This compound possesses pharmacological activity affecting the central nervous system. When administered perorally to animals, it exhibits antidepressant action. This antidepressant property is evidenced in the control of tetrabenazine-induced ptosis in mice. An oral dose of 50 mg/kg of this compound to mice intraperitoneally receiving 35 mg/kg of tetrabenazine counteracts the ptosis property of tetrabenazine.

In order that this invention be readily available to and understood by those skilled in the art the following example is supplied:

A mixture containing 21.1 g (0.10 mole) of 10,11 dihydrodibenz [b,f][1,4]oxazepin-11-one, 21.50 g (0.11 mole) of 3,4-dichlorobenzyl chloride, 8.0 g sodium hydride - 60% in mineral oil (4.80g, 0.20 mole) and 3.0 g sodium iodide in 500 ml toluene was stirred and refluxed for 16 hours and cooled. Methanol (5.0 ml) was added and the mixture was diluted with 500 ml water.

The toluene layer was separated and the aqueous layer was extracted with 300 ml chloroform followed by 300 ml ethyl acetate. The combined extracts were dried (magnesium sulfate) and concentrated to dryness in vacuo.

The residue (42 g) was dissolved in 160 ml toluene and the solution was stored at room temperature for three days and then stored in the refrigerator for an additional three days to give 6.30 g of the starting oxazepine.

The toluene filtrate was concentrated to dryness and the residue was extracted with 3 × 125 ml hot (90°) heptane. The combined heptane extracts were cooled to give 16.7 g (45%) of the product, m.p. 100°–105°.

Further recrystallization from acetonitrile gave the analytical sample, m.p. 106°–108°.

Anal. Calcd. for $C_{20}H_{13}Cl_2NO_4$: C, 64.88; H, 3.54; N, 3.79. Found: C, 64.66; H, 3.46; N, 3.95.

What is claimed is:
1. The compound of the formula:

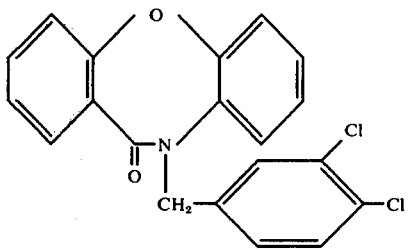

* * * * *